(12) United States Patent
Frye et al.

(10) Patent No.: US 7,582,607 B2
(45) Date of Patent: Sep. 1, 2009

(54) MUTEINS OF FIBROBLAST GROWTH FACTOR 21

(75) Inventors: Christopher Carl Frye, Bargersville, IN (US); Lihua Huang, Carmel, IN (US); Radmila Micanovic, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 259 days.

(21) Appl. No.: 11/574,332

(22) PCT Filed: Jul. 26, 2005

(86) PCT No.: PCT/US2005/026398

§ 371 (c)(1),
(2), (4) Date: Feb. 27, 2007

(87) PCT Pub. No.: WO2006/028595

PCT Pub. Date: Mar. 16, 2006

(65) Prior Publication Data

US 2008/0103096 A1    May 1, 2008

Related U.S. Application Data

(60) Provisional application No. 60/606,805, filed on Sep. 2, 2004.

(51) Int. Cl.
*A61K 38/18* (2006.01)
*C07K 14/50* (2006.01)

(52) U.S. Cl. .............................. 514/12; 514/2; 530/399

(58) Field of Classification Search ........................ None
See application file for complete search history.

(56) References Cited

U.S. PATENT DOCUMENTS 6,716,626 B1    4/2004  Itoh et al.
7,491,697 B2 *  2/2009  Beals et al. .................... 514/12

2007/0142278 A1 *  6/2007  Beals et al. .................... 514/12

FOREIGN PATENT DOCUMENTS

| WO | WO 94/26873   | 11/1994 |
|----|---------------|---------|
| WO | WO 96/05224   | 2/1996  |
| WO | WO 01/18172   | 3/2001  |
| WO | WO 01/18209   | 3/2001  |
| WO | WO 01/36640   | 5/2001  |
| WO | WO 01/38357   | 5/2001  |
| WO | WO 03/011213  | 2/2003  |
| WO | WO 03/059270  | 7/2003  |
| WO | WO 2005/113606| 12/2005 |

OTHER PUBLICATIONS

Hansen, J E, et al., "Netoglyc: Prediction of Mucin Type O-Glycosylation Sites Based on Sequence Context and Surface Accessibility", *Glycoconjugate Journal*, Lund, SE, vol. 15, No. 2, 1998, pp. 115-130.
Ciechanover, Aaron, et al., "N-terminal ubiquitnation: more protein substrates join in", Trends in Cell Biology (2004), 14(3): 103-106.
Nishimura, T., et al., "Identification of a Novel FGF, FGF-21, Preferentially Expressed in the Liver", Biochimica et Biophysica Acta (2000), 1492(1): 203-206.
Kharitonenkov, Alexei et al., "FGF-21 As a Novel Metabolic Regulator", Journal of Clinical Investigation (2005), 115(6): 1627-1635.
Blom, et al., Predication of post-translational glycosylation and phosphorylationo f proteins from the amino acid sequence, *Proteomics*, 2004, 4, 1633-1649.
Cactic, et al., Predication of post-translational glycosylation and phosphorylation of proteins from the amino acid sequence, vol. 20, 18, 2004, 3302-3307.

* cited by examiner

*Primary Examiner*—Christine J Saoud
(74) *Attorney, Agent, or Firm*—Lynn D. Apelgren

(57) ABSTRACT

The present invention relates to novel muteins of human fibroblast growth factor 21 with reduced capacity of O-glycosylation when expressed in yeast compared to wild-type human FGF-21. Both protein and the respective encoding nucleic acid species are disclosed. The invention also embodies vectors and host cells for the propagation of said nucleic acid sequences and the production of said muteins. Also disclosed are methods for treating type 2 diabetes, obesity, or metabolic syndrome.

3 Claims, No Drawings

SEQUENCE LISTING

<160> NUMBER OF SEQ ID NOS: 2

<210> SEQ ID NO 1
<211> LENGTH: 181
<212> TYPE: PRT
<213> ORGANISM: homo sapiens

<400> SEQUENCE: 1

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175
```

Pro Ser Tyr Ala Ser
            180

<210> SEQ ID NO 2
<211> LENGTH: 543
<212> TYPE: PRT
<213> ORGANISM: homo sapiens

<400> SEQUENCE: 2

Cys Ala Cys Cys Cys Ala Thr Cys Cys Thr Gly Ala Cys Thr
1               5                   10                  15

Cys Cys Ala Gly Thr Cys Cys Thr Cys Thr Cys Cys Thr Gly Cys Ala
            20                  25                  30

Ala Thr Thr Cys Gly Gly Gly Gly Cys Ala Ala Gly Thr Cys
35                  40                  45

Cys Gly Gly Cys Ala Gly Cys Gly Gly Thr Ala Cys Cys Thr Cys Thr
50                  55                  60

Ala Cys Ala Cys Ala Gly Ala Thr Gly Ala Thr Gly Cys Cys Cys Ala
65                  70                  75                  80

Gly Cys Ala Gly Ala Cys Ala Gly Ala Ala Gly Cys Cys Cys Ala Cys
            85                  90                  95

Cys Thr Gly Gly Ala Gly Ala Thr Cys Ala Gly Gly Ala Gly Gly
            100                 105                 110

Ala Thr Gly Gly Ala Cys Gly Gly Thr Gly Gly Gly Gly Gly
115                 120                 125

Cys Gly Cys Thr Gly Cys Thr Gly Ala Cys Cys Ala Gly Ala Gly Cys
130                 135                 140

Cys Cys Cys Gly Ala Ala Ala Gly Thr Cys Thr Cys Thr Gly Cys
145                 150                 155                 160

Ala Gly Cys Thr Gly Ala Ala Ala Gly Cys Cys Thr Thr Gly Ala Ala
            165                 170                 175

Gly Cys Cys Gly Gly Gly Ala Gly Thr Thr Ala Thr Thr Cys Ala Ala
            180                 185                 190

Ala Thr Cys Thr Thr Gly Gly Gly Ala Gly Thr Cys Ala Ala Gly Ala
195                 200                 205

Cys Ala Thr Cys Ala Gly Gly Thr Thr Cys Cys Thr Gly Thr Gly
210                 215                 220

Cys Cys Ala Gly Cys Gly Gly Cys Cys Ala Gly Ala Thr Gly Gly
225                 230                 235                 240

Gly Cys Cys Cys Thr Gly Thr Ala Thr Gly Gly Ala Thr Cys Gly Cys
            245                 250                 255

Thr Cys Cys Ala Cys Thr Thr Thr Gly Ala Cys Cys Thr Gly Ala
260                 265                 270

Gly Gly Cys Cys Thr Gly Cys Ala Gly Cys Thr Cys Cys Gly Gly
275                 280                 285

Gly Ala Gly Cys Thr Gly Cys Thr Thr Cys Thr Thr Gly Ala Gly Gly
290                 295                 300

Ala Cys Gly Gly Ala Thr Ala Cys Ala Ala Thr Gly Thr Thr Thr Ala
305                 310                 315                 320

Cys Cys Ala Gly Thr Cys Cys Gly Ala Ala Gly Cys Cys Cys Ala Cys
            325                 330                 335

Gly Gly Cys Cys Thr Cys Cys Cys Gly Cys Thr Gly Cys Ala Cys Cys
            340                 345                 350

Thr Gly Cys Cys Ala Gly Gly Gly Ala Ala Cys Ala Ala Gly Thr Cys

-continued

```
            355                 360                 365
Cys Cys Cys Ala Cys Ala Cys Cys Gly Gly Ala Cys Cys Cys Thr
370                 375                 380

Gly Cys Ala Cys Cys Cys Gly Ala Gly Gly Ala Cys Cys Ala Gly
385                 390                 395                 400

Cys Thr Cys Gly Cys Thr Thr Cys Cys Thr Gly Cys Cys Ala Cys Thr
        405                 410                 415

Ala Cys Cys Ala Gly Gly Cys Cys Thr Gly Cys Cys Cys Cys Cys
        420                 425                 430

Gly Cys Ala Cys Thr Cys Cys Cys Gly Gly Ala Gly Cys Cys Ala Cys
435                 440                 445

Cys Cys Gly Gly Ala Ala Thr Cys Cys Thr Gly Gly Cys Cys Cys Cys
450                 455                 460

Cys Cys Ala Gly Cys Cys Cys Cys Cys Gly Ala Thr Gly Thr Gly
465                 470                 475                 480

Gly Gly Cys Thr Cys Cys Thr Cys Gly Gly Ala Cys Cys Cys Thr Cys
        485                 490                 495

Thr Gly Ala Gly Cys Ala Thr Gly Gly Thr Gly Gly Ala Cys Cys
        500                 505                 510

Thr Thr Cys Cys Cys Ala Gly Gly Gly Cys Cys Gly Ala Ala Gly Cys
515                 520                 525

Cys Cys Cys Ala Gly Cys Thr Ala Cys Gly Cys Thr Thr Cys Cys
530                 535                 540
```

MUTEINS OF FIBROBLAST GROWTH FACTOR 21

This is the national phase application, under 35 USC 371, for PCT/US2005/026398, filed 26 Jul. 2005, which, claims the benefit, under 35 USC 119(e), of US provisional application 60/606,805, filed 2 Sep. 2004.

BACKGROUND OF THE INVENTION

1. Field of the Invention

The present invention relates to the identification of new muteins of fibroblast growth factor 21 that have reduced O-linked glycosylation when expressed in yeast.

2. Description of the Related Art

Fibroblast growth factors are large polypeptides widely expressed in developing and adult tissues (Baird et al., *Cancer Cells,* 3:239-243, 1991) and play crucial roles in multiple physiological functions including angiogenesis, mitogenesis, pattern formation, cellular differentiation, metabolic regulation and repair of tissue injury (McKeehan et al., *Prog. Nucleic Acid Res. Mol. Biol.* 59:135-176, 1998). According to the published literature, the FGF family now consists of at least twenty-three members, FGF-1 to FGF-23 (Reuss et al., *Cell Tissue Res.* 313:139-157 (2003).

Fibroblast growth factor-21 (FGF-21) has been reported to be preferentially expressed in the liver (Nishimura et al., *Biochimica et Biophysica Acta,* 1492:203-206, 2000); WO01/36640; and WO01/18172) and described as a treatment for ischemic vascular disease, wound healing, and diseases associated with loss of pulmonary, bronchia or alveolar cell function and numerous other disorders. More recently, FGF-21 has been shown to stimulate glucose-uptake in mouse 3T3-L1 adipocytes after prolonged treatment (72 h), in the presence and absence of insulin, and to decrease fed and fasting blood glucose, triglycerides, and glucagon levels in ob/ob and db/db mice and 8 week old ZDF rats in a dose-dependant manner, thus, providing the basis for the use of FGF-21 as a therapy for treating diabetes and obesity (WO03/011213).

The development of recombinant DNA technology has made possible the production of foreign products such as muteins of FGF-21 in host cells in which exogenous DNA sequences coding for those products have been introduced. The advantage of this technology is that products can be produced in high yields, in highly purified form, with low risk of contamination such as viral contamination. These recombinant techniques have been widely used for the production of recombinant proteins in prokaryotic as well as eukaryotic host cells.

However, the large-scale production of recombinant products by these techniques is still limited, due to problems of expression efficiency of these exogenous DNA sequences, due also to vector instability and to intracellular degradation of the recombinant products by the host cell in which they are made. In addition, recombinant products are often different from their natural counterparts. For example, recombinant products produced in heterologous eukaryotic hosts usually differ from their naturally-occurring counterpart in their glycosylation content. This may concern the presence versus absence of any carbohydrate structure, the localization of said carbohydrate structure on the product, as well as the nature of the carbohydrate. More specifically, it has been shown that yeast-derived recombinant products often bear additional unnatural O-glycans compared to their natural counterpart (Van den Steen, et al., *Crit. Reviews in Biochem. and Mole. Biol.* 33(3): 151-208, 1998).

The present invention solves the problem of abnormal O-glycosylation associated with yeast-derived recombinant proteins by providing FGF-21 muteins that have a reduced amount for O-glycosylation compared to wild type FGF-21 when expressed in yeast. Applicants have found that the FGF-21 muteins with reduced O-glycosylation can be produced in industrial fermentation conditions and maintain the biological activity necessary to be useful to treat subjects with disorders including, but not limited to, type II diabetes, obesity, and metabolic syndrome.

SUMMARY OF THE INVENTION

In a first embodiment, the present invention provides muteins of human FGF-21, or a biologically active peptide thereof, comprising the substitution of any amino acid except Ser or Thr for Ser 167, wherein the numbering of the amino acids is based on SEQ ID NO:1 and wherein said mutein has reduced capacity for O-glycosylation when expressed in yeast compared to wild-type human FGF-21.

A second embodiment of the present invention provides muteins of human FGF-21, or a biologically active peptide thereof, comprising the substitution of any amino acid except Ser or Thr for Ser 167, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO: 1 and wherein said mutein has reduced capacity for O-glycosylation when expressed in yeast compared to wild-type human FGF-21.

A third embodiment of the present invention provides muteins of human FGF-21, or a biologically active peptide thereof, comprising the substitution of any amino acid except Ser or Thr for Ser 167 in combination with the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152; alanine 154; glutamine 156, glycine 161, serine 163, glycine 170, or serine 172, wherein the numbering of amino acids is based on SEQ ID NO:1 and wherein said mutein has reduced capacity for O-glycosylation when expressed in yeast compared to wild-type human FGF-21.

Other embodiments are drawn to polynucleotides encoding the muteins of the first, second, and third embodiments, a vector containing said polynucleotides and a host cell carrying said vector. Another embodiment is drawn to processes for producing a polypeptide, to produce cells capable of producing said polypeptide and to produce a vector containing DNA encoding said polypeptide.

Yet another embodiment is drawn to methods of treating a patient exhibiting one or more of the following condition(s): obesity, type II diabetes, insulin resistance, hyperinsulinemia, glucose intolerance, hyperglycemia, or metabolic syndrome comprising administering to said patient in need of such treatment a therapeutically effective amount of a human FGF-21 mutein of the first, second, or third embodiment.

DETAILED DESCRIPTION OF THE INVENTION

For purposes of the present invention, as disclosed and claimed herein, the following terms are as defined below.

Human FGF-21 is a 208 amino acid polypeptide containing a 27 amino acid leader sequence. Human FGF-21 has ~79% amino acid identity to mouse FGF-21 and ~80% amino acid identity to rat FGF-21. Human FGF-21 is the preferred polypeptide template for the muteins of the present invention but it is recognized that one with skill in the art could readily make muteins based on an alternative mammalian FGF-21 polypeptide sequence.

The amino acid positions of the muteins of the present invention are determined from the mature human 181 amino acid FGF-21 polypeptide as shown below (SEQ ID NO:1):

```
1                                       10                                      20
His Pro Ile Pro Asp Ser Ser Pro Leu Leu Gln Phe Gly Gly Gln Val Arg Gln Arg Tyr 30                                      40
Leu Tyr Thr Asp Asp Ala Gln Gln Thr Glu Ala His Leu Glu Ile Arg Glu Asp Gly Thr 50                                      60
Val Gly Gly Ala Ala Asp Gln Ser Pro Glu Ser Leu Leu Gln Leu Lys Ala Leu Lys Pro 70                                      80
Gly Val Ile Gln Ile Leu Gly Val Lys Thr Ser Arg Phe Leu Cys Gln Arg Pro Asp Gly 90                                      100
Ala Leu Tyr Gly Ser Leu His Phe Asp Pro Glu Ala Cys Ser Phe Arg Glu Leu Leu Leu 110                                     120
Glu Asp Gly Tyr Asn Val Tyr Gln Ser Glu Ala His Gly Leu Pro Leu His Leu Pro Gly 130                                     140
Asn Lys Ser Pro His Arg Asp Pro Ala Pro Arg Gly Pro Ala Arg Phe Leu Pro Leu Pro 150                                     160
Gly Leu Pro Pro Ala Leu Pro Glu Pro Pro Gly Ile Leu Ala Pro Gln Pro Pro Asp Val 170                                     180
Gly Ser Ser Asp Pro Leu Ser Met Val Gly Pro Ser Gln Gly Arg Ser Pro Ser Tyr Ala

Ser
```

The corresponding DNA sequence coding for the mature human 181 amino acid FGF-21 polypeptide is (SEQ ID NO:2):

```
CACCCCATCCCTGACTCCAGTCCTCTCCTGCAATTCGGGGGCCAAGTCCG

GCAGCGGTACCTCTACACAGATGATGCCCAGCAGACAGAAGCCCACCTGG

AGATCAGGGAGGATGGGACGGTGGGGGCGCTGCTGACCAGAGCCCCGAA

AGTCTCCTGCAGCTGAAAGCCTTGAAGCCGGGAGTTATTCAAATCTTGGG

AGTCAAGACATCCAGGTTCCTGTGCCAGCGGCCAGATGGGGCCCTGTATG

GATCGCTCCACTTTGACCCTGAGGCCTGCAGCTTCCGGGAGCTGCTTCTT

GAGGACGGATACAATGTTTACCAGTCCGAAGCCCACGGCCTCCCGCTGCA

CCTGCCAGGGAACAAGTCCCCACACCGGGACCCTGCACCCCGAGGACCAG

CTCGCTTCCTGCCACTACCAGGCCTGCCCCCCGCACTCCCGGAGCCACCC

GGAATCCTGGCCCCCCAGCCCCCCGATGTGGGCTCCTCGGACCCTCTGAG

CATGGTGGGACCTTCCCAGGGCCGAAGCCCCAGCTACGCTTCC
```

Amino acids are identified using the three-letter code or alternatively are designated using the standard one letter code. Mutations are designated by the three-letter code for the original amino acid, followed by the amino acid number, followed by the three-letter code for the replacement amino acid. The numerical designations of each mutein is based on the 181 amino acid sequence of mature, wild-type, human FGF-21.

For example, a substitution for serine at position 167 (i.e. Ser167) with the non-polar/hydrophobic amino acid, alanine (Ala), is designated as Ser167Ala or S167A. In a similar fashion, the double substitution for leucine at position 118 and alanine at position 134 (Leu118, Ala134) with the sulfur containing amino acid, cysteine (Cys) is designated as Leu118Cys/Ala134Cys or L118C/A134C.

The term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, β-alanine, ornithine, etc.; and chemically synthesized compounds having properties known in the art to be characteristic of amino acids.

A human FGF-21 mutein is defined as comprising human FGF-21 in which at least one amino acid of the wild-type mature protein has been substituted by another amino acid. Examples of FGF-21 muteins are described in U.S. patent application Ser. No. 60/528,582 herein incorporated by reference. Generally speaking, a mutein possesses some modified property, structural or functional, of the wild-type protein. For example, the mutein may have enhanced or improved physical stability in concentrated solutions (e.g., less hydrophobic mediated aggregation), while maintaining a favorable bioactivity profile. The mutein may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. The mutein may have reduced O-glycosylation when expressed in yeast. Such O-glycosylation may introduce new immunological determinants on a protein and may therefore be antigenic when administered to humans; may alter the pharmacokinetic properties of a protein; and/or may affect the biological activity of a protein. Accordingly, yeast produced muteins with reduced O-glycosylation when compared to wild-type FGF-21, are less immunogenic and have a favorable pharmacokinetic profile, while maintaining biological potency. As used herein, these terms are not limiting, it being entirely possible that a given mutein has one or more modified properties of the wild-type protein.

A "therapeutically-effective amount" is the minimal amount of an active agent necessary to impart therapeutic benefit to a patient. For example, a "therapeutically-effective amount" to a patient suffering or prone to suffer or to prevent it from suffering from type II diabetes, obesity, or metabolic syndrome is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human.

Type II diabetes is characterized by excess glucose production in spite of the availability of insulin, and circulating glucose levels remain excessively high as a result of inadequate glucose clearance.

Glucose intolerance can be defined as an exceptional sensitivity to glucose.

Hyperglycemia is defined as an excess of sugar (glucose) in the blood.

Hypoglycemia, also called low blood sugar, occurs when your blood glucose level drops too low to provide enough energy for your body's activities.

Hyperinsulinemia is defined as a higher-than-normal level of insulin in the blood.

Insulin resistance is defined as a state in which a normal amount of insulin produces a subnormal biologic response.

Obesity, in terms of the human subject, can be defined as that body weight over 20 percent above the ideal body weight for a given population (R. H. Williams, Textbook of Endocrinology, 1974, p. 904-916).

Metabolic syndrome can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 or higher.

The present invention provides glycosylation muteins wherein the number and/or type of glycosylation sites is altered compared to native FGF-21. One such embodiment includes FGF-21 muteins comprising a lesser number for O-linked glycosylation sites. There is not a consensus amino acid sequence to identify the O-linked glycosylation sites, making such identification a difficult task. Normally, O-linked glycosylation occurs on the side chain of a serine or threonine residue. Once an O-linked glycosylation site is identified, amino acid substitutions to eliminate this sequence may remove an existing O-linked carbohydrate chain. O-linked glycosylation sites identified in the present invention include Ser163, Ser 164, Ser 167, Ser 172 and Ser 176. The primary site for O-glycosylation is Ser167. Applicants have discovered that eliminating the Ser167 site results in a significant reduction for O-glycosylation of the yeast expressed mutein. Although Ser167 is the preferred site of mutation to remove O-glycosylation, mutations to the other sites for O-glycosylation in human FGF-21 (Ser163, Ser164, Ser172 and Ser176) are within the scope of the present invention.

Therefore, in a first preferred embodiment, the present invention provides muteins of human FGF-21, or a biologically active peptide thereof, comprising the substitution of any amino acid except Ser or Thr for Ser 167, wherein the numbering of the amino acids is based on SEQ ID NO:1 and wherein said mutein has reduced capacity for O-glycosylation when expressed in yeast compared to wild-type human FGF-21. Preferred muteins of the first embodiment are Ser167Ala, Ser167Glu, Ser167Asp, Ser167Asn, Ser167Gln, Ser167Gly, Ser167Val, Ser167His, Ser167Lys, and Ser167Tyr.

A second embodiment of the present invention provides muteins of human FGF-21, or a biologically active peptide thereof, comprising the substitution of any amino acid except Ser or Thr for Ser 167, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO: 1 and wherein said mutein has reduced capacity for O-glycosylation when expressed in yeast compared to wild-type human FGF-21. Preferably, the phrase 'two or more' means the substitution of a cysteine for 2, 3, 4, 5, 6, 7, 8, 9, 10, 11, 12, 13, or 14 of the amino acid residues at the positions indicated above.

More preferably it means the substitution of a cysteine for 2 or 4 of the amino acid residues at the positions indicated above.

One skilled in the art will also recognize that the native cysteines, cysteine 75 and cysteine 93, could also be utilized as loci to introduce a novel disulfide bond that may impart improved properties. Specifically contemplated is the introduction of a cysteine substitution at serine 85 or phenylalanine 73, coupled with a concomitant change at either cysteine 93 or cysteine 75, respectively, wherein the latter sites are replaced with any other amino acid.

Muteins of FGF-21 with engineered disulfide bonds, in addition to the naturally occurring one at Cys75-Cys93 are described in U.S. patent application Ser. No. 60/528,582. The most preferred muteins of the second embodiment are Leu118Cys-Ala134Cys-Ser167Ala; Leu21Cys-Leu33Cys-Ser167Ala; Ala26Cys-Lys122Cys-Ser167Ala; or Leu21Cys-Leu33Cys/Leu118Cys-Ala134Cys-Ser167Ala.

A third embodiment of the present invention provides muteins of human FGF-21, or a biologically active peptide thereof, comprising the substitution of any amino acid except Ser or Thr for Ser 167 in combination with the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine145, leucine 146, isoleucine 152, alanine 154, glutamine 156, glycine 161 serine 163, glycine 170, or serine 172, wherein the numbering of the amino acids is based on SEQ ID NO:1 and wherein said mutein has reduced capacity for O-glycosylation when expressed in yeast compared to wild-type human FGF-21.

A charged amino acid is defined as a positively- or negatively-charged amino acid. A positively charged amino acid is defined to include histidine, lysine, arginine, and non-naturally occurring analogs thereof (e.g., gamma aminobutyric acid, ornithine, etc.).

A negatively charged amino acid is defined to included aspartate, glutamate, and non-naturally occurring analogs thereof (e.g., aminoadipic acid). A polar but uncharged amino acid is defined to include serine, threonine, asparagine, glutamine, and non-naturally occurring analogs thereof. Preferred muteins of the third embodiment are Gln54Glu-Ser167Ala, Leu139Glu-Ser167Ala, Ala145Glu-Ser167Ala, Leu146Glu-Ser167Ala, Ile152Glu-Ser167Ala, Gln156Glu-Ser167Ala, Ser163Glu-Ser167Ala, and Ile152Glu-Ser163Glu-Ser167Ala.

Further embodiments of the present invention provide muteins of human FGF-21, or a biologically active peptide thereof, comprising a combination of the first embodiment of the present invention, the second embodiment of the present invention and the third embodiment of the present invention wherein said mutein has reduced capacity for O-glycosylation when expressed in yeast compared to wild-type human FGF-21.

Although the embodiments of the present invention concern muteins of FGF-21 with reduced capacity for O-glycosylation when expressed in yeast compared to wild-type human FGF-21, maintaining the biological potency of the muteins as compared to wild-type FGF-21 is an important factor of consideration as well. Therefore, the biological potency of the muteins of the present invention is defined by the ability of the muteins to affect glucose uptake as measured in the in vitro 3T3-L1 cell assay (Example 2) and/or the lowering of plasma glucose levels, as well as, plasma triglycerides, as measured in vivo in the ob/ob mouse assay (Example 3).

The muteins of FGF-21 administered according to this invention may be generated and/or isolated by any means known in the art. The most preferred method for producing the mutein is through recombinant DNA methodologies and is well known to those skilled in the art. Such methods are described in *Current Protocols in Molecular Biology* (John Wiley & Sons, Inc.), which is incorporated herein by reference.

Additionally, the preferred embodiments include a biologically active peptide derived from the mutein described herein and that such a peptide will contain at least one of the substitutions described, will exhibit reduced capacity for O-glycosylation compared to the corresponding non-mutated peptide, and will possess biological activity, . This biological activity is defined by the ability of the peptide to affect glucose uptake as measured in the in vitro 3T3-L1 cell assay (Example 2) and/or the lowering of plasma glucose levels, as well as, plasma triglycerides, as measured in vivo in the ob/ob mouse assay (Example 3). The peptide may be produced by any means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., *Proc. Natl. Acad. Sci* (USA) 85:2324-2328 (1988), and *J. Cell. Phys. Suppl.* 5:101-106 (1987). For example, it is known that dipeptidyl peptidase IV (DPP-IV) is a serine type protease involved in inactivation of neuropeptides, endocrine peptides, and cytokines (Damme et al. *Chem. Immunol.* 72: 42-56, (1999)). The N-terminus of FGF-21 (HisProIlePro) contains two dipeptides that could potentially be substrates to DPP-IV, resulting in a fragment of FGF-21 truncated at the N-terminus by up to 4 amino acids. Unexpectedly, this fragment of wild-type FGF-21 has been demonstrated to retain biological activity (Table 1), thus, muteins of the present invention truncated at the N-terminus by up to 4 amino acids in combination with the amino acid substitutions of any of the embodiments of the present invention. In addition, applicants have discovered that truncation of 5 amino acids or greater from the N-terminus negatively impacts biological activity.

The present invention also encompasses polynucleotides encoding the above-described muteins that may be in the form of RNA or in the form of DNA, which DNA includes cDNA, genomic DNA, and synthetic DNA. The DNA may be double-stranded or single-stranded. The coding sequences that encode the muteins of the present invention may vary as a result of the redundancy or degeneracy of the genetic code.

The polynucleotides that encode for the muteins of the present invention may include the following: only the coding sequence for the mutein, the coding sequence for the mutein and additional coding sequence such as a functional polypeptide, or a leader or secretory sequence or a pro-protein sequence; the coding sequence for the mutein and non-coding sequence, such as introns or non-coding sequence 5' and/or 3' of the coding sequence for the mutein. Thus the term "polynucleotide encoding a mutein" encompasses a polynucleotide that may include not only coding sequence for the mutein but also a polynucleotide, which includes additional coding and/or non-coding sequence.

The present invention further relates to variants of the described polynucleotides that encode for fragments, analogs and derivatives of the polypeptide that contain the indicated substitutions. The variant of the polynucleotide may be a naturally occurring allelic variant of the human FGF-21 sequence, a non-naturally occurring variant, or a truncated variant as described above. Thus, the present invention also includes polynucleotides encoding the muteins described above, as well as variants of such polynucleotides, which variants encode for a fragment, derivative or analog of the disclosed mutein that exhibit reduced capacity for O-glycosylation compared to the corresponding non-mutated fragment, deriviative, or analog. Such nucleotide variants include deletion variants, substitution variants, truncated variants, and addition or insertion variants as long as at least one of the indicated amino acid substitutions of the first, second, or third embodiments is present.

The polynucleotides of the present invention will be expressed in a host cell after the sequences have been operably linked to an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. Preferably, the host cell is a fungal or yeast cell.

Yeast cells used for expressing the muteins of the present invention include *Pichia pastoris, Saccharomyces cerevisiae, Schizosaccharomyces pombe*, and *Pichia angust*. The yeast host cells contain suitable vectors with expression control sequences, such as promoters, including 3-phosphoglycerate kinase or other glycolytic enzymes, and an origin of replication, termination sequences and the like as desired. The preferred yeast host of the present invention is *Pichia pastoris* wherein the expression vector is integrated into the host chromosomal DNA. *Aspergillus niger, Trichoderma reesei*; and *Schizophyllum commune*, are examples of fungi hosts, although others may also be employed as a matter of choice.

The vectors containing the polynucleotide sequences of interest (e.g., the muteins of FGF-21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step(s) selected will depend, for example, on the nature of the production process used for the muteins of FGF-21.

The FGF-21 mutein-containing compositions should be formulated and dosed in a fashion consistent with good medical practice, taking into account the clinical condition of the patient, the site of delivery of the FGF-21 mutein composition, the method of administration, the scheduling of administration, and other factors known to practitioners. The "therapeutically effective amount" of the FGF-21 mutein for purposes herein is thus determined by such considerations.

The pharmaceutical compositions of the FGF-21 muteins of the present invention may be administered by any means known in the art that achieve the generally intended purpose to treat type II diabetes, obesity, or metabolic syndrome. The preferred route of administration is parenteral, defined herein as referring to modes of administration that include intravenous, intramuscular, intraperitoneal, intrastemal, subcutaneous, and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein an FGF-21 mutein is present in an amount that is effective to achieve the desired medical effect for treatment type II diabetes, obesity, or metabolic syndrome. While individual needs may vary from one patient to another, the determination of the optimal ranges of effective amounts of all of the components is within the ability of the clinician of ordinary skill.

The muteins of FGF-21 of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [*Remington's Pharmaceutical Sciences* 16th edition (1980)]. The muteins of the present invention may be combined with a pharmaceutically acceptable buffer, and the pH adjusted to provide acceptable stability, and a pH acceptable for administration. Moreover, the muteins of the present invention may be placed into a container selected from the group consisting of a vial, a cartridge, a pen delivery device, a syringe, intravenous administration tubing and an intravenous administration bag, wherein the container is a unit dose container.

For parenteral administration, the FGF-21 muteins are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF-21 mutein, as determined by good medical practice and the clinical condition of the individual patient. The appropriate dose of an FGF-21 mutein administered will result in lowering blood glucose levels and increasing energy expenditure by faster and more efficient glucose utilization, and thus is useful for treating type 2 diabetes, obesity and metabolic syndrome.

Furthermore, FGF-21 did not induce hypoglycemia in lean ZDF rats when compared to rats dosed with insulin (WO03/011213). This data indicates that FGF-21 affects plasma glucose levels in an insulin independent manner, suggesting that FGF-21 muteins of the present invention may also be useful in the treatment of Type I diabetes.

In another aspect of the present invention, muteins of human FGF-21 herein described, or a biologically active peptide thereof, are used as a medicament.

In yet another aspect of the present invention, an effective amount of the muteins of FGF-21 herein described, or a biologically active peptide thereof, are used in the manufacture of a medicament for the treatment or prevention of one or more conditions selected from type II diabetes, obesity, or metabolic syndrome.

Having now described the present invention in detail, the same will be more clearly understood by reference to the following examples, which are included herewith for purposes of illustration only and are not intended to be limiting of the invention.

All patents and publications referred to herein are expressly incorporated by reference.

EXAMPLE 1

Expression and Purification of FGF-21 Muteins in Yeast

FGF-21 muteins are expressed in yeast, such as *Pichia pastoris, Pichia methanolica* or *Saccharomyces cerevisiae*. For production in *Pichia pastoris* a commercially available system (Invitrogen, Carlsbad, Calif.) uses vectors with the powerful AOX1 (alcohol oxidase) promoters to drive high-level expression of recombinant proteins. Alternatively, vectors that use the promoter from the GAP gene (glyceraldehyde-3-phosphate dehydrogenase) are available for high level constitutive expression. The multi-copy *Pichia* expression vectors allows one to obtain strains with multiple copies of the gene of interest integrated into the genome. Increasing the number of copies of the gene of interest in a recombinant *Pichia* strain can increase protein expression levels. Yet another yeast expression system is *Saccharomyces cerevisiae*. Expression vectors contain the promoter and enhancer sequences from the GAL1 gene. The GAL1 promoter is one of the most widely used yeast promoters because of its strong transcriptional activity upon induction with galactose.

Analytical characterization (mass spectrum analyses) indicates that the FGF-21 expressed in *Pichia pastoris* is truncated (four amino acid removal at the wild-type N-terminus). When assayed in the mouse 3T3-L1 adipocyte assay (see Example 2), this truncated variant of FGF-21 stimulates glucose uptake at the same level as wild-type FGF-21 (Table 1).

EXAMPLE 2

Glucose Uptake in Mouse 3T3-L1 Adipocytes

3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, two days after cells reached confluency (referred as day 0), cells are exposed to differentiation medium (DM) containing 10% fetal bovine serum, 10 μg/ml of insulin, 1 μM dexamethasone, and 0.5 μM isobutylmethylxanthine, for 48 h. Cells then are maintained in post differentiation medium containing 10% fetal bovine serum, and 10 μg/ml of insulin.

Glucose Transport Assay—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM NaPO$_4$, 0.9 mM CaCl$_2$, 0.9 mM MgSO$_4$, pH 7.4) warmed to 37° C. and containing 0.2% BSA, incubated in Leibovitz's L-15 medium containing 0.2% BSA for 2 h at 37° C. in room air, washed twice again with KRP containing, 0.2% BSA buffer, and incubated in KRP, 0.2% BSA buffer in the absence (Me$_2$SO only) or presence of wortmannin for 30 min at 37° C. in room air. Insulin is then added to a final concentration of 100 nM for 15 min, and the uptake of 2-deoxy-D-[$^{14}$C]glucose is measured for the last 4 min. Non-specific uptake, measured in the presence of 10 μM cytochalasin B, is subtracted from all values. Protein concentrations are determined with the Pierce bicinchoninic acid assay. Uptake is measured routinely in triplicate or quadruplicate for each experiment.

In vitro potency is normalized to the in vitro activity of wild-type FGF-21, which is given a designation of 1.0 and used as a positive control. The in vitro potency of muteins of FGF-21 of the present invention is compared to wild-type FGF-21 in Table 1. As indicated in Table 1, the muteins of the present invention maintained biological potency to various degrees compare to wild-type FGF-21.

TABLE 1

| FGF-21 Mutein | Expression System | In vitro Potency* |
|---|---|---|
| Wild-type | E. coli | 1.0 |
| ΔHPIP Truncated Wild-type** | Yeast | 0.9 |
| ΔHPIP L118C, A134C | Yeast | 0.2 |
| ΔHPIP L118C, A134C, S167A | Yeast | 0.2 |

*potency is a relative value based on the activity of E. coli produced wild-type FGF-21
**truncated by 4 amino acids at the N-terminus

EXAMPLE 3

Ob/Ob Mouse Model

A study in an obesity model using male ob/ob mice is done to monitor plasma glucose levels and triglyceride levels after treatment with FGF-21, compared to vehicle and insulin control groups. The test groups of male ob/ob mice (7 weeks old) are injected with vehicle alone (0.9% NaCl), or FGF-21 mutein (0.125 mg/kg) subcutaneously (0.1 mL, once daily) for seven days. Blood is collected by tail clip bleeding on day 7, one hour after the last compound injection and plasma glucose levels are measured using a standard protocol. The ability of the FGF-21 muteins to lower plasma glucose levels as compared to the vehicle control is shown in Table 2. The data in Table 2 indicates that muteins of the present invention lowered plasma glucose levels as compared to vehicle control. The ability of the FGF-21 muteins to lower triglyceride levels as compared to the vehicle control is shown in Table 3.

TABLE 2

| FGF-21 Mutein | Plasma Glucose levels as % of Control |
|---|---|
| Wild-type | 62% |
| L118C-A134C | 70% |
| L118C-A134C-S167A | 62% |

TABLE 3

| FGF-21 Mutein | Triglyceride Levels (mg/dL) |
|---|---|
| Vehicle Control | 210 |
| Wild-type | 116*** |
| L118C-A134C | 137** |
| L118C-A134C-S167A | 153* |

P value vs. vehicle control:
*p ≤ 0.05;
**p ≤ 0.02;
***p ≤ 0.001

EXAMPLE 4

Pharmaceutical Stability of FGF-21 Muteins

The stability of the FGF-21 muteins of the present invention is analyzed under simulated physiological and pharmaceutical formulation conditions. To simulate physiological conditions, the mutein is analyzed for stability in PBS at room temperature (RT) at a target protein concentration of 10 mg/ml, pH 7.4. Solubility/physical stability of the muteins in PBS is considered satisfactory if recovery of protein following preparation resulted in >90% recovery at RT as determined by size-exclusion and/or reversed-phase chromatography. As indicated in Tables 4 and 5, the muteins of the present invention meet this criteria.

It is anticipated that pharmaceutical formulation of a mutein of the present invention will likely be a preserved multi-use formulation, thus, compatibility with a common preservative is analyzed. To test for formulation compatibility, a preservative, m-cresol, (3 mg/mL final concentration, a concentration usually sufficient to meet European Pharmacopia B criteria for preservative effectiveness under neutral pH conditions), is added at room temperature to a solution containing the mutein at approximately 10 mg/ml in PBS, pH 7.4. Physical stability in the presence of preservative is initially accessed by determining protein recovery of the main chromatographic peak after reversed-phase and size exclusion chromatography at RT. Furthermore, the extent of aggregation as measured by DLS (dynamic light scattering) at 37° C. is shown as the average diameter of particles in the presence of m-cresol after two hours, compared to wild-type FGF-21. A larger average diameter corresponds to an increased degree protein association and/or aggregation. The preservative compatibility (as a function average diameter of particulates) of the muteins of the first and second embodiments of the present invention compared to wild-type FGF-21 is shown in Table 4. Wild-type protein is expressed in *E. coli*, while the muteins are expressed in yeast (*Pichia pastoris*).

Muteins of the present invention that are stable in PBS and compatible with preservative are designated to have enhanced or improved pharmaceutical properties as compared to wild-type FGF-21. As shown in Tables 4, the preferred muteins of the present invention that have enhanced pharmaceutical properties as compared to wild-type FGF-21 are L118C-A134C and L118C-A134C-S167A.

TABLE 4

| FGF-21 Mutein | Average Particulate Diameter (nm)* |
|---|---|
| Experiment #1 | |
| Wild-type FGF-21 | 1356 |
| Experiment #2 | |
| Wild-type FGF-21 | 813 |
| L118C-A134C | 7 |
| L118C-A134C-S167A | 7 |

*Average Particulate diameter represents a protein solution at a target conc. of 10 mg/ml, m-cresol at 3 mg/ml, after 2 hours incubation at 37° C.

EXAMPLE 5

Analysis of O-Glycosylation

FGF-21 muteins are expressed in *Pichia pastoris* and are purified from the culture broth by HPLC (Waters 2695) using a Zorbax, 330-SB C8, 4.6×50 mm, 3.5 μm particle Column at 40° C. (Move Phase C: 0.1% TFA in 10% ACN and 90% H2O, D: 0.1% TFA in ACN).

O-glycosylation levels of the purified muteins of FGF-21 are measured by standard LC/MS analysis. The percentage for O-glycosylation for representative muteins is shown in Table 5 compared to human wild type FGF-21. The O-glycosylation levels of the preferred mutein L118C-A134C-S167A is only 3% compared to >60% for wild type FGF-21 or the mutien L118C-A134C, clearly demonstrating that the S167A mutien significantly reduces the level of O-glycosylation.

TABLE 5

| FGF-21 Mutein | % O-Glycosylation |
|---|---|
| Wild-type | 62% |
| L118C-A134C | 63% |
| L118C-A134C-S167A | 3% |

---

We claim:

1. A mutein of human FGF-21 consisting of human FGF-21 containing 1 engineered disulfide bond and a substitution of Ser 167 with Ala, wherein the numbering of amino acids is based on SEQ ID NO:1 and said mutein is Δ(His1Pro2Ile3Pro4)-Leu118Cys-Ala134Cys-Ser167Ala-human FGF-21.

2. A pharmaceutical composition comprising a therapeutically effective amount of the mutein of claim 1 and a pharmaceutically acceptable carrier.

3. A method for treating a patient suffering from obesity or type II diabetes, comprising administering to said patient in need of such treatment a therapeutically effective amount of the human FGF-21 mutein of claim 1.

* * * * *